United States Patent [19]

Hoffman, Jr.

[11] Patent Number: 4,497,810

[45] Date of Patent: Feb. 5, 1985

[54] THIATRIAZINE DIOXIDES AS GASTRIC ANTI-SECRETORY AGENTS

[75] Inventor: Jacob M. Hoffman, Jr., North Wales, Pa.

[73] Assignee: Merck & Co., Inc., Rahway, N.J.

[21] Appl. No.: 541,834

[22] Filed: Oct. 14, 1983

[51] Int. Cl.$^3$ .................. C07D 285/00; C07D 417/12; C07D 417/06; A61K 31/54

[52] U.S. Cl. .......................................... 514/222; 544/7

[58] Field of Search ............................ 544/7; 424/246

[56] References Cited

U.S. PATENT DOCUMENTS

| 3,435,031 | 3/1969 | Whitehead | 544/7 |
|---|---|---|---|
| 3,817,993 | 6/1974 | Franke | 544/7 |
| 3,915,688 | 10/1975 | Franke | 71/90 |
| 4,007,175 | 2/1977 | Franke | 544/7 |

FOREIGN PATENT DOCUMENTS

| 25113 | 8/1979 | European Pat. Off. . |
|---|---|---|
| 37482 | 4/1980 | European Pat. Off. . |
| 71051 | 7/1981 | European Pat. Off. . |
| 73442 | 8/1981 | European Pat. Off. . |
| 73443 | 3/1983 | European Pat. Off. . |
| 2026625 | 12/1971 | Fed. Rep. of Germany . |
| 2943703 | 10/1979 | Fed. Rep. of Germany . |
| 3016825 | 5/1980 | Fed. Rep. of Germany . |
| 3134140 | 8/1981 | Fed. Rep. of Germany . |
| 3134141 | 8/1981 | Fed. Rep. of Germany . |
| 3143381 | 11/1981 | Fed. Rep. of Germany . |
| 3134145 | 11/1981 | Fed. Rep. of Germany . |
| 113006 | 5/1975 | German Democratic Rep. . |
| 142338 | 6/1980 | German Democratic Rep. . |

*Primary Examiner*—John M. Ford
*Attorney, Agent, or Firm*—Gabriel Lopez; Hesna J. Pfeiffer

[57] ABSTRACT

There are disclosed novel 1,2,4,6-thiatriazine-1,1-dioxides and related compounds which are connected to a substituted phenyl or heterocyclic group through a linear or cyclic connecting group. Processes are provided for the preparation of such compounds. The compounds are useful for the suppression of gastric acid secretions in mammals and compositions for such uses are also disclosed.

9 Claims, No Drawings

THIATRIAZINE DIOXIDES AS GASTRIC ANTI-SECRETORY AGENTS

BACKGROUND OF THE INVENTION

Inhibitors of gastric acid secretion functioning by antagonism of the histamine H2-receptor are effective antiulcer agents. Structurally, such compounds are typically viewed as molecules having three substituents or fragments; i.e., A-B-C, each of which can independently affect the antisecretory activity. The "A" portion may be a substituted or unsubstituted aromatic or heteroaromatic group such as are disclosed in, for example, U.S. Pat. No. 3,950,333 to Durant et al, U.S. Pat. No. 4,128,658 to Price et al and Belgian Pat. No. 867,106 (Derwent Abstract 84065A/47).

The central, or "B" portion, may be a connecting chain joined to A such as $A-CH_2SCH_2CH_2-$, $AOCH_2CH_2CH_2$, or A-(m-phenylene)- as disclosed in the aforementioned patents as well as in European Pat. No. 3,640 to Jones et al (Derwent Abstract 61827 B/34).

The remaining terminal substituent "C" is structurally distinct from either the A and B portions and may be, for example, a substituted guanidine, a substituted 1,1-diamino ethylene, or a 3,5-diamino-1-alkyl triazole as disclosed in the aforementioned U.S. Patents to Durant et al and Price et al as well as in Belgian Pat. No. 875,846 (Derwent Abstract 79110 B/44).

The present invention is directed to unique "C" moieties which confer antisecretory activity when combined with the A-B molecular fragments comprising these antiulcer agents. These novel, structural "C" elements are the 1,2,4,6-thiatriazine-1,1-dioxide groups. Incorporation of these groups into the A-B molecular fragments affords compounds that exhibit significant antisecretory activity.

SUMMARY OF THE INVENTION

This invention is concerned with 1,2,4,6-thiatriazine-1,1-dioxide compounds which are connected to a substituted phenyl or heterocyclic moiety through a linear or cyclic connecting group.

DESCRIPTION OF THE INVENTION

The compounds of this invention are best realized in the following structural formula:

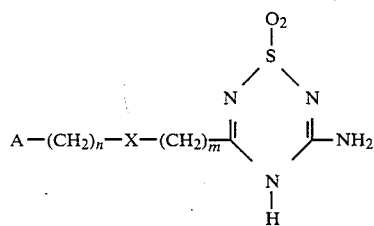

I wherein:
n is 0 or 1;
m is 2 to 4;
X is oxygen, sulfur, or methylene;
Ⓐ is phenylene or a 5- or 6-membered heterocycle containing one to three heteroatoms selected from oxygen, sulfur or nitrogen, which may optionally have a benzo ring fused thereon and which may be substituted with diloweralkylaminoloweralkyl, or guanidino wherein the alkyl groups contain 1 to 8 carbon atoms; and,
the pharmaceutically acceptable salts thereof.

Illustrative of Ⓐ in Formula I are such compounds as, for example, furan, thiophene, pyrrole, oxazole, oxadiazole, thiadiazole, thiazole, triazole, pyrazole, imidazole, pyridine, pyrimidine, pyrazine, and the like, and the fused benzo derivatives thereof such as benzofuran, benzoxazole, benzimidazole, and the like.

Preferred variations of Ⓐ are those wherein Ⓐ is furan, imidazole, thiazole, oxazole, thiophene, triazole, thiadiazole, oxadiazole, or benzofuran.

The compounds according to the invention readily form physiologically acceptable salts. Such salts include salts with inorganic acids such as hydrochlorides, hydrobromides, sulfates, nitrates and phosphates. Particularly useful salts of organic acids are formed with aliphatic mono- or dicarboxylic or sulfonic acids. Examples of such salts are acetates, maleates fumarates, tartrates, citrates, benzoates, succinates, methane sulfonates, and isethionates. The compounds and their salts may also form hydrates and solvates. In addition, the nitrogen atoms in group Ⓐ may also form quaternary salts and N-oxides.

It will also be appreciated by those skilled in the art that the compounds of this invention will have a tautomeric isomerism about the nitrogen atoms in the thiatriazine ring including the exo-imino structures shown below:

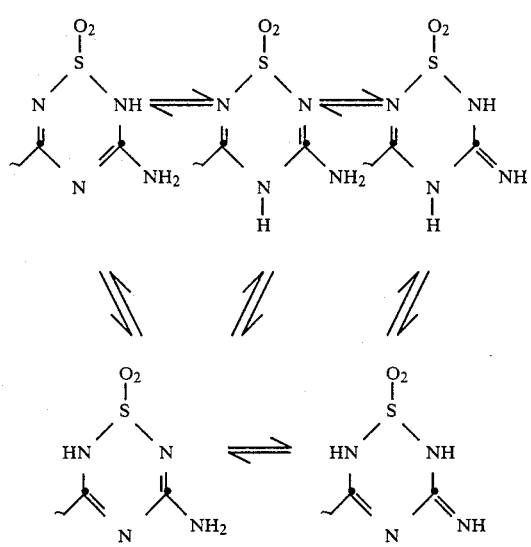

All of the various tautomeric structures of the instant compounds are intended to be included in this invention.

As stated above, the compounds represented by Formula I have been found to have pharmacological activity in the animal body as antagonists to certain actions of histamine which are not blocked by "antihistamines" such as mepyramine. For example, they have been found to inhibit selectively the histamine-stimulated secretion of gastric acid in the stomach of chronic fistula dogs at doses of from 2.5 to 250 mg per kilogram intravenously or orally from 5 to 250 mg per kilogram. Similarly, the action of these compounds is demonstrated by their antagonism to the effects of histamine on other tissues which are not affected by histamine H1 antagonists. An example of such tissue is the isolated guinea-pig right atrium.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water, and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 15 mg to about 0.4 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit gastric acid secretory activity. The route of administration may be orally or parenterally.

Preferably, each daily dosage will contain the active ingredient in an amount of from about 1 mg to about 500 mg, most preferably from about 20 mg to about 200 mg given in a single dose or multiple divided doses.

For therapeutic use, the pharmacologically active compounds of the present invention will normally be administered as a pharmaceutical composition comprising as the single or as an essential active ingredient at least one such compound in the basic form or in the form of an addition salt with a pharmaceutically acceptable acid and in association with a pharmaceutical carrier therefor. Such addition salts include those mentioned above.

Other pharmacologically active compounds may, in certain cases, be included in the composition. For example, it may be appropriate to combine the instant compound or compounds with anticholinergic agents such as propantheline; H1 antihistamines such as mepyramine, pyribenzamine, chlorpheniramine, and the like; or prostanoids.

Advantageously the composition will be made up in a dosage unit form appropriate to the desired mode of administration such as, for example, a tablet, capsule or injectable solution.

The compounds of this invention can be prepared as illustrated in the following Reaction Schemes wherein preferred reactants are shown to more clearly illustrate the process of the invention.

REACTION SCHEME A

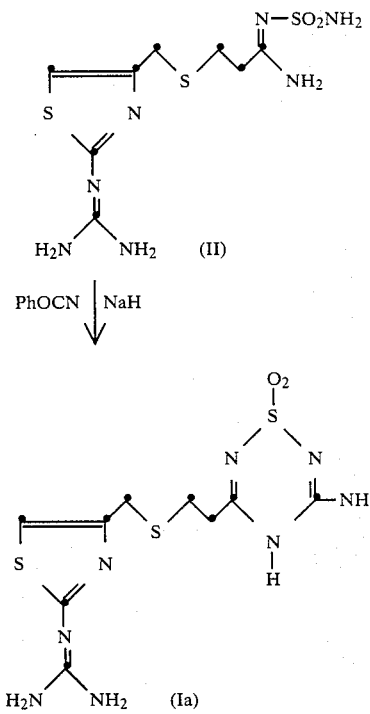

REACTION SCHEME B

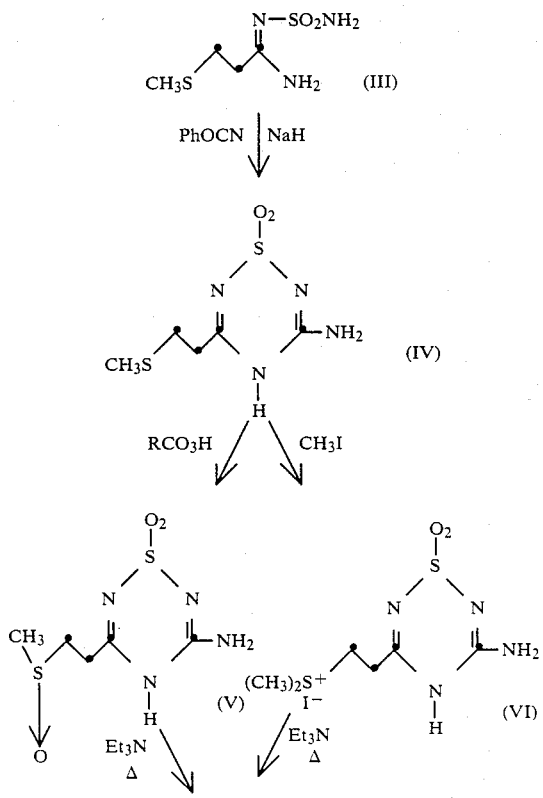

-continued
REACTION SCHEME B

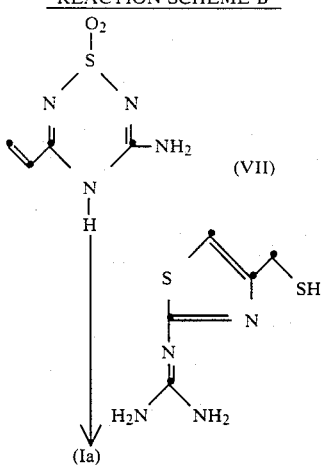

As shown in Reaction Scheme A, sulfamylamidine (II), which can be prepared by the methods disclosed in U.S. Pat. No. 4,283,408, is condensed with phenyl cyanate in the presence of sodium hydride to afford a compound (Ia) of Formula I.

In Reaction Scheme B, sulfide (III), prepared from the reaction of an alkylimidate with a sulfamide, is condensed with phenyl cyanate in the presence of sodium hydride to afford thiatriazine dioxide (IV). Reacting thiatriazine dioxide (IV) in the presence of m-chloroperbenzoic acid (R=m-ClPh) produces thiatriazine dioxide sulfoxide (V) which is then treated with an excess of a hindered amine base such as a tertiary amine (e.g., triethyl amine) to afford vinyl-thiatriazone dioxide (VII).

Alternatively, thiatriazine dioxide (IV) can be reacted with methyliodide to obtain the thiatriazine dioxide sulfonium salt (VI) which is then treated with an excess of a hindered base to afford vinyl-thiatriazine dioxide (VII).

Reaction of vinyl-thiatriazine dioxide (VII) with heterocyclic component (VIII) affords compound (Ia) of Formula I.

The following examples are provided in order that the invention might be more fully understood, but they are not to be construed as being limitative of the invention. Unless otherwise indicated, all temperatures are in degrees Celsius.

EXAMPLE 1

3-Amino-5-{2-[(2-guanidino-4-thiazolyl)methylthio]ethyl}-1,2,4,6-thiatriazine-1,1-dioxide Sodium hydride in mineral oil (60%, 0.40 gm, 10 mmol) was added to a solution of N-sulfamyl-3-[(2-guanidino-4-thiazolyl)methylthio]propionamidine (3.37 gm, 10 mmol) in dry dimethylformamide (10 ml) and dry tetrahydrofuran (40 ml) under nitrogen and the resultant mixture warmed at 70° C. for one hour. This mixture was cooled and a solution of phenylcyanate (1.2 gm, 10 mmol) in dry THF (20 ml) was added dropwise. This mixture was warmed at 60° C. for one hour and then 60% sodium hydride in mineral oil (0.40 gm, 10 mmol) was added and the reaction mixture stirred at 60° C. for 16 hours. This solution was cooled, diluted with diethyl ether to give a gummy precipitate. The solvents were decanted and the residue dissolved in water. This aqueous solution was acidified with dilute HCl, filtered, extracted with 5% methanol/chloroform, and the water solvent removed under vacuum. The residual solid was dissolved in methanol, filtered to removed salts, and the alcohol solution was concentrated to a small volume and diluted with diethylether to give a yellow powder (4.3 gm). This solid was chromatographed on silica gel eluting with 20% methanol/chloroform saturated with ammonia to remove unreacted starting material and then 20% methanol/chloroform containing 1% glacial acetic acid to give purified product (1.3 gm). This material was further purified by chromatography on silica gel, eluting with 20% methanol/acetonitrile to give 0.63 gm of solid title compound as a solvate with acetic acid and acetonitrile, mp 175°–192° C.

The following representative compounds are prepared in an analogous manner by this method:

3-Amino-5-{2-[(2-pyridyl)methylthio]ethyl}1,2,4,6-thiatriazine-1,1-dioxide from N-sulfamyl-3-[(2-pyridyl)methylthio]propionamidine which is disclosed in Japanese Pat. No. J57026663 (Derwent Abs. 22898 E/12).

3-Amino-5-{4-[(2-guanidino-4-thiazolyl)methylthio]butyl}-1,2,4,6-thiatriazine-1,1-dioxide from N-sulfamyl-5-(2-guanidino-4-thiazolyl)pentanoamidine (valeroamidine) which is disclosed in U.S. Pat. No. 4,283,408 (Derwent Abs. 65965 C/38).

3-Amino-5-{2-[(5-dimethylaminomethyl-2-furanyl)methylthio]ethyl}-1,2,4,6-thiatriazine-1,1-dioxide from N-sulfamyl-3-[(5-dimethylaminomethyl-2-furanyl)methylthio]propionamidine which is prepared by the method disclosed in U.S. Pat. No. 4,283,408 starting with ethyl 3-{(5-dimethylaminomethyl-2-furanyl)methylthio}propionimidate which is disclosed in Japanese Pat. No. J55115877 (Derwent Abs. 74415 C/42).

3-Amino-5-}2-[(3-dimethylaminomethyl)benzylthio]ethyl}-1,2,4,6-thiatriazine-1,1-dioxide from N-sulfamyl-3-[(3-dimethylaminomethyl)benzylthio]propionamidine which is prepared by the method disclosed in U.S. Pat. No. 4,283,408 starting with ethyl 3-[(3-dimethylaminomethyl)benzylthio]propionimidate which is disclosed in Japanese Pat. No. J55115860 (Derwent Abs. 74408 C/42).

EXAMPLE 2

3-Amino-5-[2-(methylthio)ethyl]-1,2,4,6-thiatriazine-1,1-dioxide

To a solution of N-sulfamyl-3-(methylthio)propionamidine (4.9 gm, 25 mmol) in dry tetrahydrofuran (75 ml) under nitrogen there was added 60% sodium hydride in mineral oil (1.0 gm, 25 mmol). This mixture was warmed at 60° C. for ½ hour as a copious precipitate formed. To this suspension, a solution of phenylcyanate (3.0 gm, 25 mmol) in dry THF was added dropwise giving a homogeneous solution. After ½ hour, additional 60% sodium hydride in mineral oil (1.0 gm, 25 mmol) was added and the resultant solution warmed at 50° C. for 20 hours. The reaction mixture was diluted with diethyl ether and the precipitate collected by filtration. This precipitate was dissolved in water, acidified with dilute HCl, filtered and the aqueous solution extracted with 3% methanol/chloroform and then the water removed under vacuum. The residue was extracted with acetonitrile, filtered, and the extract evaporated to give crude product (2.0 gm). This material was chromatographed on silica gel and eluted with 5–10% methanol/chloroform. Upon concentration of the appropriate fractions, the product crystallized, (1.4 gm), m.p. 243°–246° C.

EXAMPLE 3

3-Amino-5-[2-(methylsulfinyl)ethyl]-1,2,4,6-thiatriazine-1,1-dioxide

To a solution of 3-amino-5-[2-(methylthio)ethyl]-1,2,4,6-thiatriazine-1,1-dioxide (1.22 gm, 5.5 mmol) in warm methanol (20 ml) there was added dropwise a solution of 80% pure m-chloroperbenzoic acid (1.2 gm, 5.6 mmol) in chloroform (20 ml). The product crystallized from solution during the addition and was collected by filtration and washed with diethyl ether to give 1.27 gm of pure product, m.p. 180°–182° C.

EXAMPLE 4

3-Amino-5-[2-(dimethylsulfonium)ethyl]-1,2,4,6-thiatriazine-1,1-dioxide iodide To a solution of 3-amino-5-[2-(methylthio)ethyl]-1,2,4,6-thiatriazine-1,1-dioxide (333 mg, 1.5 mmol) in methanol (8 ml) there was added excess methyl iodide (0.9 ml). This reaction mixture was sealed in a flask and stirred at room temperature for two days. The precipitated product was collected by filtration, washed with methanol and ether to give pure product (460 ml), m.p. 276°–278° C.

What is claimed is:

1. A compound having the formula:

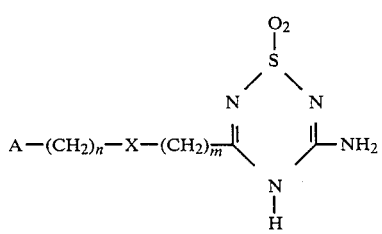

(I)

wherein:
n is 0 or 1;
m is 2 to 4;
X is oxygen, sulfur, or methylene;
Ⓐ is phenylene, furan, thiophene, pyrrole, oxazole, oxadiazole, thiadiazole, thiazole, triazole, pyrazole, imidazole, pyridine, pyrimidine, pyrazine, benzofuran, benzoxazole, or benzimidazole, which may be substituted with diloweralkylaminoloweralkyl, or guanidino wherein the alkyl groups contain 1 to 8 carbon atoms;
and, the pharmaceutically acceptable salts thereof.

2. The compound of claim 1 wherein Ⓐ is phenylene, furan, thiophene, pyrrole, oxazole, oxadiazole, thiazole, thiadiazole, triazole, pyrazole, imidazole, pyridine, pyrimidine, pyrazine or benzofuran.

3. A compound of claim 1 which is: 3-amino-5-{2-[(2-guanidino-4-thiazolyl)-methylthio]ethyl}-1,2,4,6-thiatriazine-1,1-dioxide.

4. A method for suppressing gastric acid secretions in an animal with excess gastric acid secretions which comprises administering to said animal an antisecretorily effective amount of a compound of claim 1.

5. A composition useful for suppressing gastric acid secretions in an animal with excess gastric acid secretions which comprises an inert carrier and an antisecretorily effective amount of a compound of claim 1.

6. A compound having the formula:

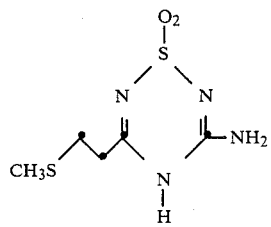

(IV)

7. A compound having the formula:

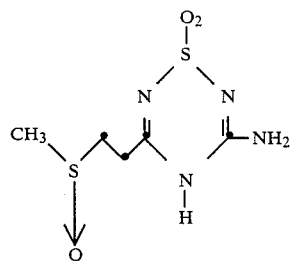

(V)

8. A compound having the formula:

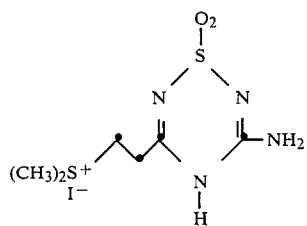

(VI)

9. A compound having the formula:

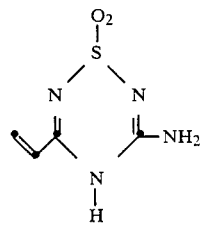

(VII)

* * * * *